(12) United States Patent
Gill

(10) Patent No.: US 9,719,818 B1
(45) Date of Patent: Aug. 1, 2017

(54) FLUID METER SYSTEM

(71) Applicant: Meredith E. Gill, Lakeway, TX (US)

(72) Inventor: Meredith E. Gill, Lakeway, TX (US)

(*) Notice: Subject to any disclaimer, the term of this patent is extended or adjusted under 35 U.S.C. 154(b) by 231 days.

(21) Appl. No.: 14/634,344

(22) Filed: Feb. 27, 2015

Related U.S. Application Data

(60) Provisional application No. 61/945,506, filed on Feb. 27, 2014.

(51) Int. Cl.
*G01F 15/06* (2006.01)
*G01F 1/00* (2006.01)
*G01D 9/00* (2006.01)

(52) U.S. Cl.
CPC ............ *G01F 1/00* (2013.01); *G01D 9/005* (2013.01)

(58) Field of Classification Search
USPC ....................................... 73/272 A
See application file for complete search history.

(56) References Cited

U.S. PATENT DOCUMENTS

| | | | | |
|---|---|---|---|---|
| 5,656,784 A | * | 8/1997 | Butch | G01F 1/54 702/100 |
| 6,053,054 A | * | 4/2000 | Wusterbarth | G01F 1/66 73/861.28 |
| 6,109,100 A | * | 8/2000 | Buckley | A61J 9/00 604/76 |
| 6,588,613 B1 | * | 7/2003 | Pechenik | A61J 11/001 215/11.1 |
| 7,333,020 B2 | * | 2/2008 | Cohen | A61B 5/038 340/573.1 |
| 7,896,835 B2 | * | 3/2011 | Dahan | A61B 5/4288 604/73 |
| 8,413,502 B2 | * | 4/2013 | Zemel | A61B 5/4288 73/198 |
| 2008/0039778 A1 | * | 2/2008 | Goldie | A61B 5/038 604/67 |

\* cited by examiner

*Primary Examiner* — Clayton E Laballe
*Assistant Examiner* — Warren K Fenwick
(74) *Attorney, Agent, or Firm* — Richard G. Eldredge; Eldredge Law Firm

(57) ABSTRACT

A fluid intake system includes a fluid meter having a body with a hole extending the length of the body, the hole being configured to receive the fluid conduit therethrough, a sensor carried within the body and operably associated a computer, the sensor being configured to detect the flowrate of the fluid passing through the fluid conduit and relay a detected fluid flow to the computer, and a display operably associate with the computer, the display being configured to display a numerical value of the fluid flow rate.

11 Claims, 3 Drawing Sheets

FLUID METER SYSTEM

BACKGROUND

1. Field of the Invention

The present invention relates generally to fluid meters.

2. Description of Related Art

It should be understood that hospitals and other facilities require a patient to consume a specific amount of fluids during the recovery process. As such, the fluid intake of the patient is closely monitored by the nurse. There are times when the amount of fluid intake is confused due to human error.

It should be understood that it is also desired for most persons to consume a certain amount, e.g., 4 gallons of water to remain hydrated. Keeping track of the amount of fluid consumption per day can become a burdensome feat, nearly impossible for most persons.

As such, there is a need for a fluid system adapted to monitor the fluid intake of a person.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
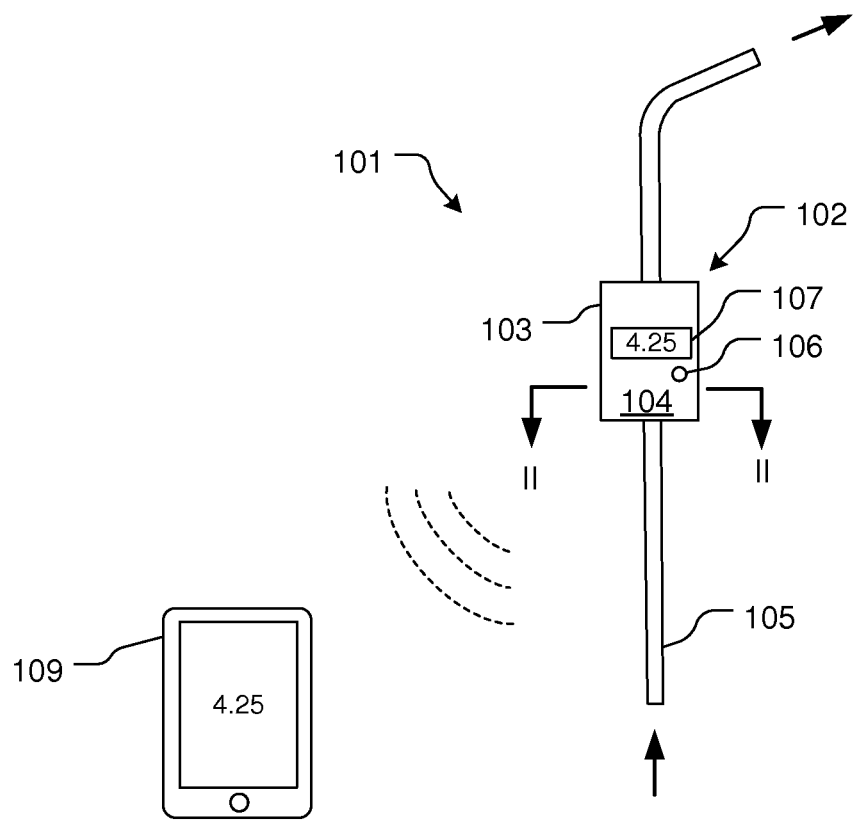
FIG. 1 is a front view of a fluid system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional fluid systems. Specifically, the system of the present application includes a meter configured to measure the amount of fluid consumed by the user. To achieve this feature, the meter can be either directly attached to the fluid source or have a conduit, e.g., a straw as means to channel fluid through the meter. The system is further provided with a display that provides visual indication of the amount of fluid consumed. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system and method of use are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Referring now to the drawings wherein like reference characters identify corresponding or similar elements throughout the several views, FIG. 1 depicts a front view of a fluid system 101 in accordance with a preferred embodiment of the present application. It will be appreciated that system 101 overcomes at least one of the above-listed problems commonly associated with the conventional fluid systems.

Figure 2:
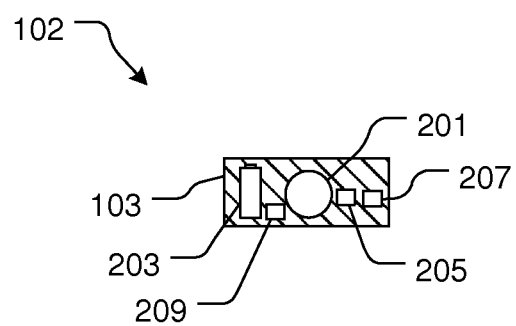
FIG. 2 is a cross-sectional view of the fluid system of FIG. 1 taken at II-II.

In the contemplated embodiment, system 101 preferably includes one or more of fluid meter 102 having a body 103 configured to receive a conduit 105, e.g., a straw, therethrough. Thus, in the contemplated embodiment, the straw passes directly through the interior of the body 103 via hole 201, as illustrated in FIG. 2.

System 101 is further provided with flow sensor 205, a computer 207 and a power source 203 all disposed within body 103. During use, a switch 106 in the form of a button and operably associated with the computer 207 activates sensor 205, which in turn monitors the amount of fluid passing through conduit 105 and provides visual indication of the fluid passage via a display 107 carried on the body 103 and visible via a front surface 104.

Another unique feature believed characteristic of the present application is the use of a mobile device 109 in communication with meter 102. This feature allows monitoring of the fluid intake via the mobile device. To achieve this feature, system 101 is further provided with a transceiver 209 in data communication with the computer 207 and sensor 205. In the exemplary embodiment, the mobile device 109 is a smartphone; however, it will be appreciated that alternative embodiments could include different types of mobile devices such as wrist bands, tablets, laptops, and the like.

During use, as depicted with a plurality of arrows, the fluid from a fluid reservoir (not shown) passes through the conduit 105, through body 103, and exits conduit 105 to the user. As the fluid passes through the conduit 105, the computer and sensors operably associated with fluid meter 102 are adapted to determine the flowrate and amount of fluid intake. Thereafter, the calculated fluid intake is displayed on the display and/or relayed to a mobile device. These features enable the user or third party to monitor the amount of fluid intake.

FIG. 2 illustrates a cross-sectional view of fluid meter 102. As depicted, the body 103 include an elongated hole 201 that extends the entire longitudinal length of body 103. During use, the user will slide the fluid conduit 105 through hole 201. It will be appreciated that in one contemplated embodiment, the opening has substantially the same inner diameter as the outer diameter of conduit 105 such that a snug fit is created therebetween.

Figure 3:
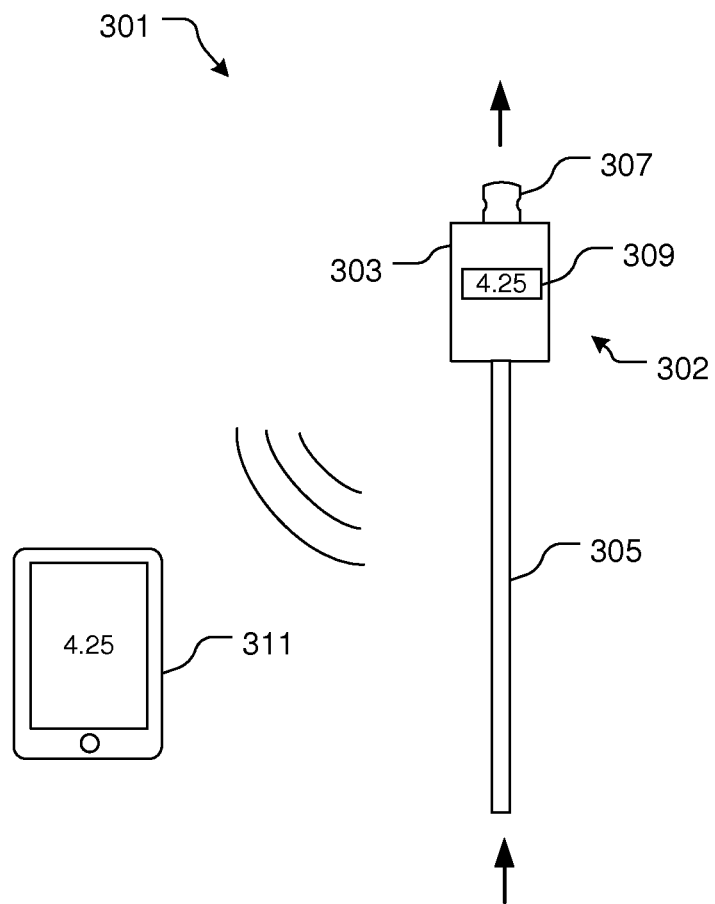
FIG. 3 is a front view of a fluid system in accordance with an alternative embodiment of the present application.

In FIG. 3, an alternative embodiment of system 101 is shown. As depicted, system 301 includes a meter 302 having a body 303 configured to securely engage with a conduit 305. It will be appreciated that system 301 is substantially similar in form and function to system 101 and incorporates one or more of the features discussed therein, namely, a computer, sensor, transmitter/receiver, display 309 and means to communicate with a mobile device 311. However, in this embodiment, system 301 includes a nipple 307 secured to body 303, which can be a disposable nipple and thereby removed (e.g., threadingly engaged) with body 303. It will be appreciated that the nipple 307 allows the user to drink from the conduit without having to come into contact therewith. In the contemplated embodiment, conduit 305 attaches to body 303 and the fluid passes through the body and out nipple 307 in a similar manner discussed above with respect to system 101.

Figure 4:
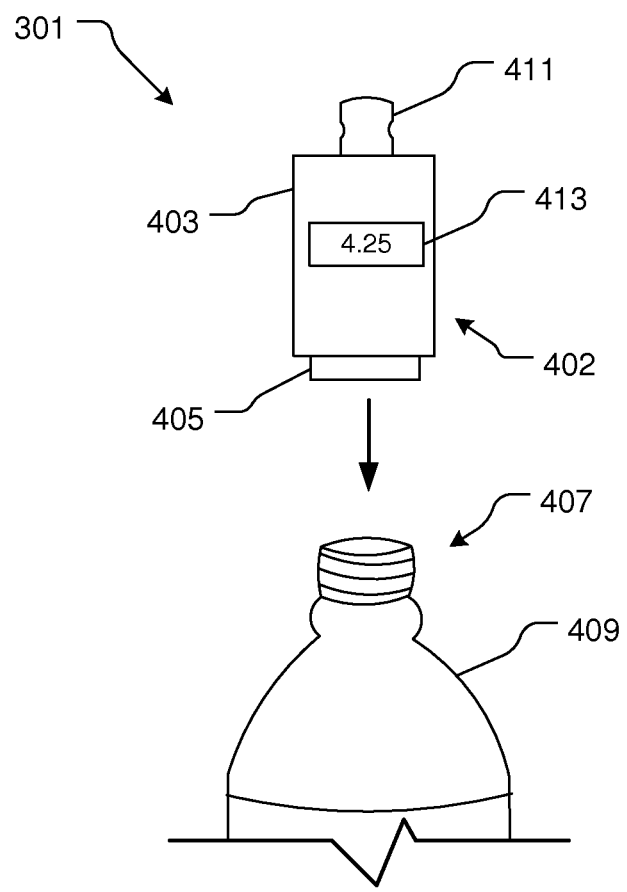
FIG. 4 is a front view of a fluid system in accordance with an alternative embodiment of the present application.

FIG. 4 is yet another embodiment of the present application. It will be appreciated that system 401 is substantially similar in form and function to system 301 and incorporates one or more of the features discussed therein, namely, a computer, sensor, transmitter/receiver, display, and means to communicate with a mobile device.

In the exemplary embodiment, system 401 includes a meter 402 having a body 403 with an attachment device 405 configured to receive a top portion 407 of a fluid bottle 409. In the contemplated embodiment, attachment device 405 is configured to threadingly engage with the top of the bottle 409; however, it will be appreciated that alternative embodiments could include other types of quick-release fastening means to secure the meter 402 to the bottle 409.

During use, the fluid from bottle 409 passes through attachment device 405, body 403 and through a nipple 411. Thereafter, the fluid intake is shown on a display 413 and/or a mobile device, as discussed herein.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A fluid intake system adapted to receive a straw and configured to monitor a fluid passing through the straw, the fluid system comprising:
   a fluid meter having:
   a body with a hole extending the length of the body, the hole being configured to receive the straw there through;
   a sensor carried within the body and operably associated a computer, the sensor being configured to detect the flowrate of the fluid passing through the straw and relay a detected fluid flow to the computer; and
   a display operably associated with the computer, the display being configured to display a numerical value of the fluid flow rate;
   wherein the fluid meter is removable from the straw via the hole.

2. The system of claim 1, further comprising:
   a switch operably associated with the computer and configured to activate the fluid meter.

3. The system of claim 1, further comprising:
   a transceiver operably associated with the computer and configured to transmit the fluid flow rate to a mobile device.

4. The system of claim 3, wherein the mobile device is configured to display the flow rate of the fluid passing through the straw.

5. The system of claim 3, wherein the mobile device is a smartphone.

6. A fluid intake system adapted to engage with a bottle and configured to monitor a fluid passing through a fluid conduit, the fluid system comprising:
   a fluid meter having:
   a body with the fluid conduit disposed therein and extending the length of the body;
   a sensor carried within the body and operably associated a computer, the sensor being configured to detect the flowrate of the fluid passing through the fluid conduit and relay a detected fluid flow to the computer;
   a display operably associated with the computer, the display being configured to display a numerical value of the fluid flow rate; and
   a cap secured to the body and configured to attach the body to the bottle in place of a bottle cap, the cap having:
   an opening wherein the fluid conduit extends and is in fluid communication with fluid from the bottle.

7. The system of claim 6, further comprising:
   a switch operably associated with the computer and configured to activate the fluid meter.

8. The system of claim 6, further comprising:
   a transceiver operably associated with the computer and configured to transmit the fluid flow rate to a mobile device.

9. The system of claim 8, wherein the mobile device is configured to display the flow rate of the fluid passing through the fluid conduit.

10. The system of claim 8, wherein the mobile device is a smartphone.

11. The system of claim 6, further comprising:
    a nipple attached to the body and configured to fluidly engage with the fluid conduit.

* * * * *